(12) United States Patent
Luo et al.

(10) Patent No.: US 10,342,777 B2
(45) Date of Patent: Jul. 9, 2019

(54) CAFFEOYLQUINIC ACID-RICH EXTRACT AND PREPARATION AS WELL AS USE THEREOF

(71) Applicant: Macau University of Science and Technology, Macau (CN)

(72) Inventors: Pei Luo, Macau (CN); Zhifeng Zhang, Chengdu (CN); Hao Zhang, Chengdu (CN)

(73) Assignee: MACAU UNIVERSITY OF SCIENCE AND TECHNOLOGY, Macau (CN)

( * ) Notice: Subject to any disclaimer, the term of this patent is extended or adjusted under 35 U.S.C. 154(b) by 0 days.

(21) Appl. No.: 14/872,198

(22) Filed: Oct. 1, 2015

(65) Prior Publication Data

US 2017/0095443 A1 Apr. 6, 2017

(51) Int. Cl.
*A61K 31/357* (2006.01)
*A61K 31/216* (2006.01)
*A61K 36/28* (2006.01)

(52) U.S. Cl.
CPC .......... *A61K 31/357* (2013.01); *A61K 31/216* (2013.01); *A61K 36/28* (2013.01)

(58) Field of Classification Search
CPC .................................................. A61K 31/357
USPC ........................................................ 514/456
See application file for complete search history.

(56) References Cited

FOREIGN PATENT DOCUMENTS

CN 104892419 * 5/2015 ........... A61K 31/357

OTHER PUBLICATIONS

Zhang, CN 104892419, Abstract STN Accession No. 2015:1452436.*
Pan, CN 1616381, Abstract STN Accession No. 2005:1265544.*
Sun, CN 102650626, Abstract STN Accession No. 2012:1280450.*
Zhang et al. Faming Zhuanli Shenqing (2015), CN 104892419A Sep. 9, 2015.*
Zhang, Rapid Communications in Mass Spectrometry (2007), 21(18), 2971-2984.*
Li, PLoS One (2013), 8(11), e74490/1-e74490/10, 10 pp.*
Park, Archives of Pharmacal Research (2010), 33(11), 1703-1720.*
Anders, et al. "Biology, Metastatic Patterns, and Treatment of Patients with Triple-Negative Breast Cancer" Clin. Breast Cancer, vol. 9, pp. 1-19 (Jun. 2009).
Barretina, et al. "The Cancer Cell Line Encyclopedia enables predictive modelling of anticancer drug sensitivity" Nature, vol. 483, pp. 603-608 (Mar. 2012).
Borner, et al. "Immunological quantitation of phospholipid/CA2+-dependent protein kinase of human mammary carcinoma cells: Inverse relationship to estrogen receptors" Int. J. Cancer, vol. 40, pp. 344-348 (1987).
Brenton, et al. "Molecular Classification and Molecular Forecasting of Breast Cancer: Ready for Clinical Application?" Journal of Clinical Oncology, vol. 23, No. 29, pp. 7350-7360 (2005).
Carey, et al. "Triple-Negative breast cancer: disease entity or title of convenience?" Nature Reviews Clinical Oncology 7, pp. 683-692 (2010).
Chmura, et al. "In vitro and in vivo activity of Protein Kinase C Inhibitor Chelerythrine Chloride Induces Tumor Cell Toxicity and Growth Delay in vivo" Clinical Cancer Research, vol. 6, pp. 737-742 (2000).
Gandhi, et al. "Protection against in vivo focal myocardial ischemia/reperfusion injury-induced arrhythmias and apoptosis by hesperidin" Free Radic. Res. vol. 23(9), pp. 817-827 (2009).
Gottlieb, R.A., "Cell death pathways in acute ischemia/reperfusion injury" J. Cardiovasc. Pharmacol. Ther. vol. 16 (3-4), pp. 233-238 (Sep.-Dec. 2011).
Crown, et al. "Emerging Targeted therapies in triple-negative breast cancer" Annals of Oncology vol. 23 (Supp. 6) pp. 56-65 (2012).
Dent, et al. "Pattern of metastatic spread in triple-negative breast cancer" Breast Cancer Res. Treat, vol. 115, pp. 423-428 (2009).
Dent, et al. "Triple-Negative Breast Cancer: Clinical Features and Patterns of Recurrence" American Association for Cancer Research, pp. 1-7 (2007).
Fabbro, et al. Epidermal Growth Factor Binding and Protein Kinase C Activities in Human Breast Cancer Cell Lines: Possible Quantitative Relationship, Cancer Research, vol. 46, pp. 2720-2725 (Jun. 1986).
Foulkes, et al. "Triple-Negative Breast Cancer" N. Engl. J. Med, vol. 363, pp. 1938-1948 (2010).
Frankel, et al. "Protein Kinase C α is a marker for antiestrogen resistance and is involved in the growth of tamoxifen resistant human breast cancer cells" Breast Cancer Res. Treat, vol. 104, pp. 165-179 (2007).
Garg, et al. "Protein Kinase C and cancer: what we know and what we do not" Oncogene, vol. 33(45), pp. 5225-5237 (2014).
Gordge, et al. "Elevation of Protein Kinase A and Protein Kinase C activities in malignant as compared with normal human breast tissue" European Journal of Cancer, vol. 32A, No. 12, pp. 2120-2126 (1996).
Herbert, et al. "Chelerythrine is a potent and specific inhibitor of Protein Kinase C" Biochemical and Biophysical Research Communications, vol. 172, No. 3, pp. 993-999 (1990).
Hsu, et al. "Definition of PKC-alpha, CDK6, and MET as therapeutic targets in triple-negative breast cancer" Cancer Res. vol. 74(17), pp. 4822-4835 (2014).

(Continued)

*Primary Examiner* — Nizal S Chandrakumar
(74) *Attorney, Agent, or Firm* — Renner Kenner Greive Bobak Taylor & Weber

(57) ABSTRACT

A caffeoylquinic acid-rich extract obtained from *Erigeron multiradiatus* and a method for producing the same. A caffeoylquinic acid-rich extract includes at least 15% by weight of a mixture of certain caffeoylquinic acids. The extract with the mixture of caffeoylquinic acids is highly efficacious in treating and preventing myocardial ischemia or myocardial ischemia reperfusion injuries. A method for treating or preventing a disease caused by myocardial ischemia or myocardial ischemia reperfusion includes administering a therapeutically effective amount of the caffeoylquinic acid-rich extract to a subject. Pharmaceutical compositions including the caffeoylquinic acid-rich extract are also disclosed.

3 Claims, 7 Drawing Sheets

(56) References Cited

OTHER PUBLICATIONS

"GLOBOCAN 2012: Estimated Cancer Incidence, Mortality and Prevalence Worldwide in 2012" International Agency for Research on Cancer, http:globocan.iarc.fr/Default.aspx, Retrieved Sep. 16, 2015, pp. 1-2 (2015).

Kang, J. "Protein Kinase C (PKC) Isozymes and Cancer" New Journal of Science, vol. 2014, pp. 1-36 (2014).

Kemeny-Beke, et al. "Apoptotic response of uveal melanoma cells upon treatment with chelidonine, sanguinarine and chelerythrine" Cancer letters, vol. 237, pp. 67-75 (2006).

Kumar, et al. "A benzophenanthridine alkaloid, chelerythrine induces apoptosis in vitro in a Dalton's lymphoma" Journal of Cancer Research and Therapeutics, vol. 9, No. 4, pp. 693-700 (2013).

Lee, et al. "The Nucleoside analog sangivamycin induces apoptotic cell death in breast carcinoma MCF7/Adriamycin-resistant cells via protein kinase Cδ and JNK activation" Journal of Biological Chemistry, vol. 282, No. 20, pp. 15271-15283 (2007).

Liedtke, et al. "Response to Neoadjuvant Therapy and Long-term survival in Patients with triple-negative breast cancer" Journal of Clinical Oncology, vol. 26, No. 8, pp. 1275-1281 (2008).

Lonne, et al. "PKC-alpha expression is a marker for breast cancer aggressiveness" Molecular Cancer, vol. 9, pp. 1-14 (2010).

Lonne, et al. "Protein Kinase Cδ Supports Survival of MDA-MB-231 Breast Cancer Cells by Suppressing the ERK1/2 Pathway" Journal of Biological Chemistry vol. 284, No. 48, pp. 33456-33465 (2009).

Malikova, et al. "The effect of chelerythrine on cell growth, apoptosis, and cell cycle in human normal and cancer cells in comparison with sanguinarine" Cell Biology and Toxicology, Vo. 22, Issue 6, pp. 439-453 (2006).

Masso-Welch, et al. "Altered expression and localization of PKC eta in human breast tumors" Breast Cancer Research and Treatment, vol. 68, Issue 3, pp. 211-223 (2001).

Mayer, et al. "New Strategies for triple-negative breast cancer-Deciperhing the heterogeneity" Clic. Cancer Res. vol. 20(4), pp. 782-790 (2014).

Mochly-Rosen, et al. "Protein Kinase C, an elusive therapeutic target?" Nat. Rev. Drug Discov. vol. 11(12), pp. 937-957 (2012).

O'Brian, et al. "Elevated Protein Kinase C Expression in Human Breast Tumor Biopsies relative to normal breast tissue" Cancer Research, Vo. 49, pp. 3215-3217 (1989).

Prat, et al. "Decosntructing the molecular portraits of breast cancer" Molecular Oncology, Vo. 5, pp. 5-23 (2011).

Rosse, et al. "PKC and the control of localized signal dynamics" Nature Reviews Molecular Cell Biology, vol. 11, pp. 103-112 (2010).

Schmidt, et al. "Rho GTPases regulate PKR2/PKN2 to control entry into mitosis and exit from cytokinesis" The EMBO Journal, vol. 26, pp. 1624-1636 (2007).

Sun, et al. "Protein Kinase C-zeta is required for epidermal growth factor-induced chemotaxis of human breast cancer cells" Cancer Res. vol. 65(4), pp. 1433-1441 (2005).

Tam, et al. "Protein Kinase C alpha is a central signaling node and therapeutic target for breast cancer stem cells" Cancer Cell. vol. 24(3), pp. 347-364 (2013).

Tomao, et al. "Triple-negative breast cancer: new perspectives for targeted therapies" OncoTargets and Therapy, pp. 177-193 (2015).

Tonetti, et al. "Stable Transfection of protein kinase C alpha cDNA in hormone-dependent breast cancer cell lines" British Journal of Cancer, vol. 83(6), pp. 782-791 (2000).

Tonetti, et al. "Elevated protein kinase C alpha expression may be predictive of tamoxifen treatment failure" British Journal of Cancer, vol. 88, pp. 1400-1402 (2003).

White, et al. "Extranuclear ER-alpha is associated with regression of T47D PKCalpha-overexpressing, tamoxifen-resistant breast cancer" Molecular Cancer, vol. 12(34), pp. 1-13 (2013).

Turner, et al. "Integrative molecular profiling of triple negative breast cancers identifies amplicon drivers and potential therapeutic targets" Oncogene, vol. 29(14), pp. 2013-2023 (2010).

Vichai, et al. "Sulforhodamine B colorimetric assay for cytotoxicity screening" Nature Protocols, vol. 1, pp. 1112-1116 (2006).

Vucenik, et al. "Inositol hexphosphate (IP6) blocks proliferation of human breast cancer cells through a PKCδ-dependent increase in p27KIP1 and decrease in retinoblastoma protein (pRb) phoshphorylation" Breast Cancer Research and Treatment, vol. 91, Issue 1, pp. 35-45 (2005).

Whyte, et al. "PKC zeta regulates cell polarisation and proliferation restriction during mammary acinus formation" Journal of Cell Science, vol. 123, pp. 3316-3328 (2010).

Yang, et al. "Activation of the RAF/Mitogen-Activated Protein/Extracellular Signal-Regulated Kinase Kinase/Extracellular Signal-Regulaed Kinase Pathway Mediates Apoptosis Induced by Chelerythrine in Osteoscarcoma" Human Cancer Biology, vol. 14(20), pp. 6396-6404 (2008).

Yokoyama, et al. "PKCδ and MAPK mediate G1 arrest induced by PMA in SKBR-3 breast cancer cells" Biochemical and Biophysical Research Communications, vol. 327, pp. 720-726 (2005).

Zeidan, et al. "A novel role for protein kinase Cδ-mediated phosphorylation of acid sphingomyelinase in UV light-induced mitochondrial injury" FASEB Journal, pp. 183-193 (2007).

* cited by examiner

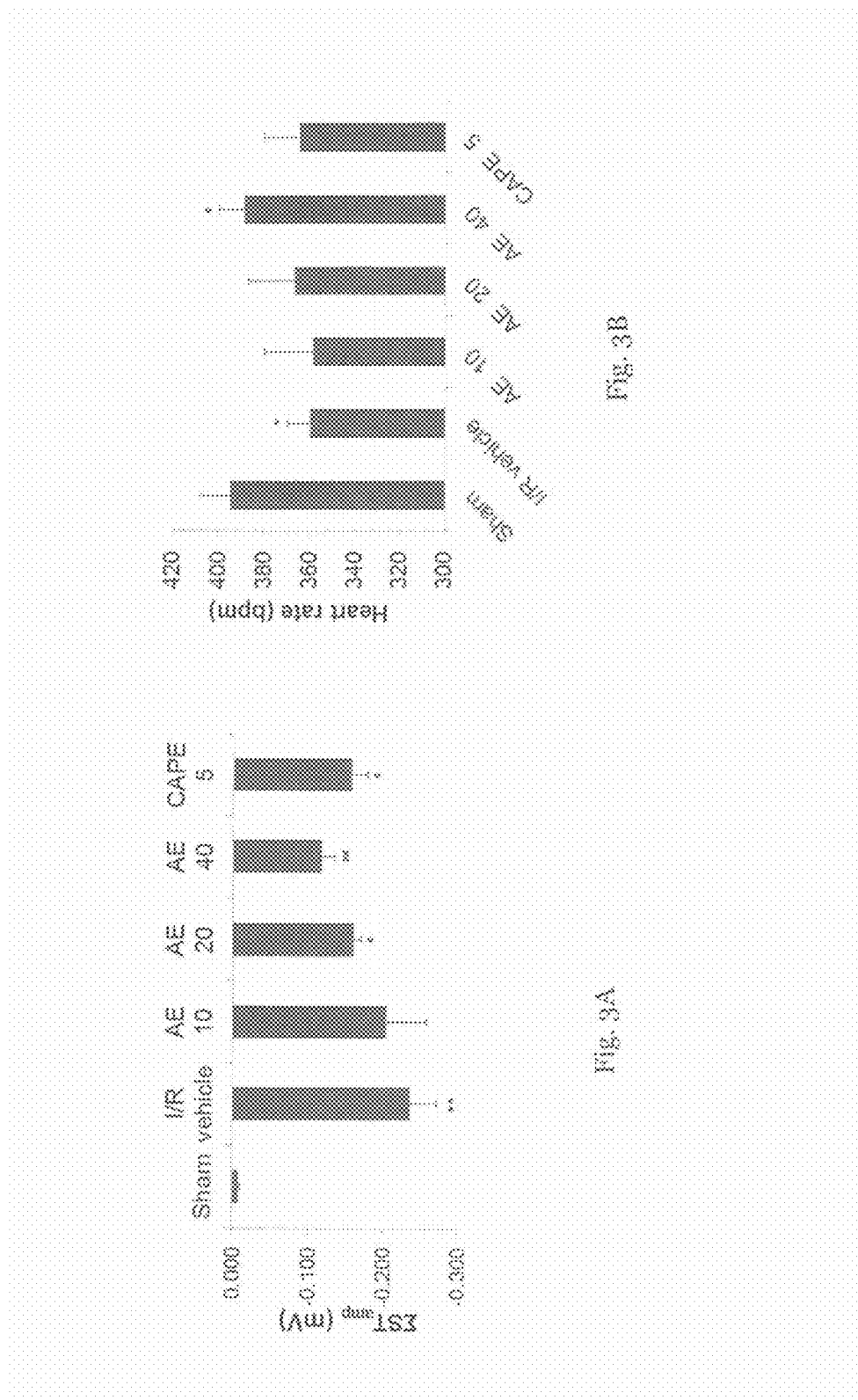

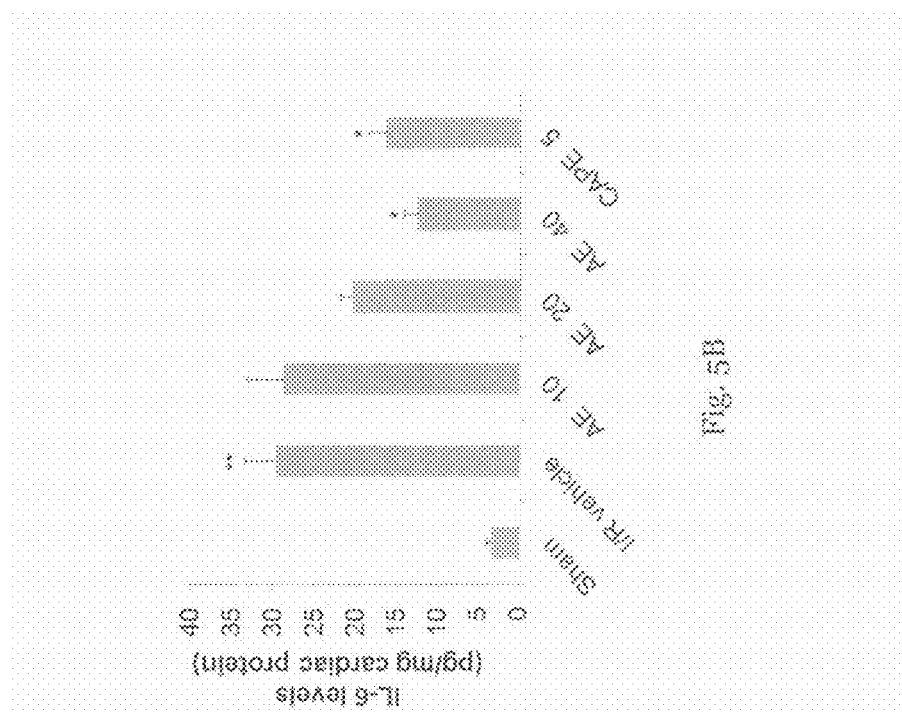
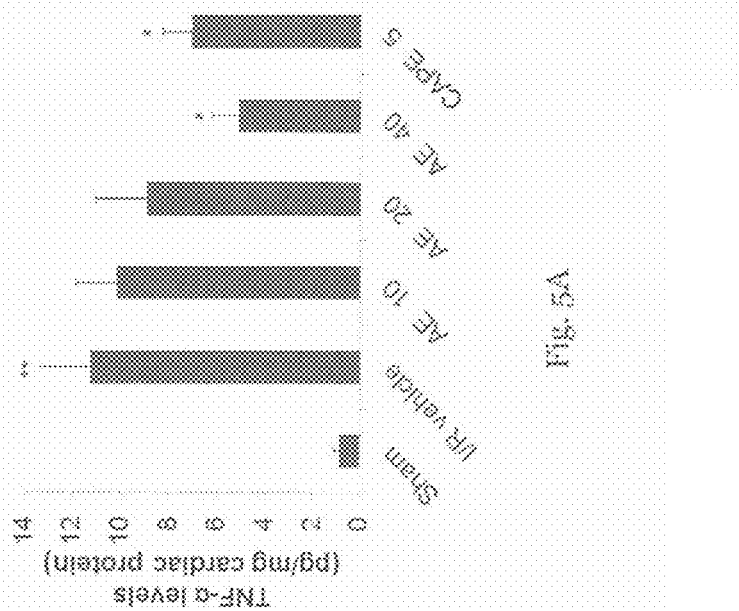

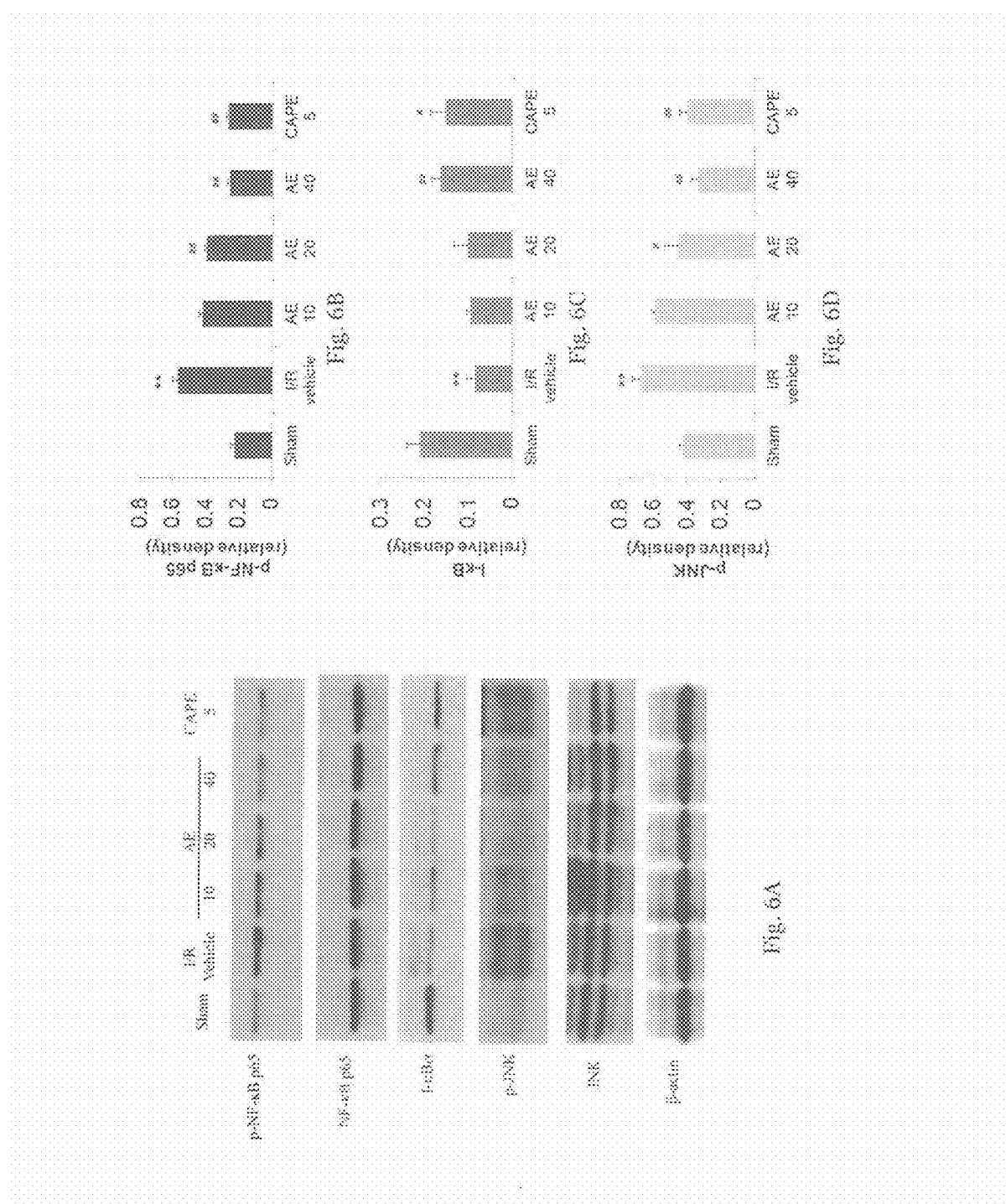

CAFFEOYLQUINIC ACID-RICH EXTRACT AND PREPARATION AS WELL AS USE THEREOF

TECHNICAL FIELD

The present invention relates to a caffeoylquinic acid-rich extract obtained from *Erigeron multiradiatus* and a method for producing the same. The present invention also refers to a method for treating or preventing a disease, and, in particular, an injury caused by myocardial ischemia or myocardial ischemia reperfusion. Still further, a pharmaceutical formulation comprising said extract is provided.

BACKGROUND OF THE INVENTION

Mechanisms underlying myocardial ischemia and reperfusion injury (also referenced as "I/R" injury) were extensively studied but are, unfortunately, neither completely known nor completely explained and understood today.

Respective pathogenesis was demonstrated to at least include inflammation, endothelial dysfunction, mitochondrial damage, cardio myocyte apoptosis and necrosis as well as involvement of reactive oxygen species. For example, the production of cytokines seems to play an important role in producing and developing acute myocardial ischemia. Within hours after the blood reflow to ischemic myocardium, cytokines seems to be secreted locally. Furthermore, inflammatory mediators are expected to be released which aggravates a possible reperfusion injury of myocardial cells. During I/R, inflammatory cytokines might modulate myocardial survival by various mechanisms including stimulation of hypertrophy and fibrosis, impairment of myocardial contractile function, induction of apoptosis and stimulation of genes involved in myocardial remodeling. Pro-inflammatory cytokines such as TNF-α (Tumor necrosis factor alpha) and IL-6 (Interleukin 6) are commonly used biomarkers contribute to up-regulation of cell-adhesion molecules, cardiac functional depression and myocardial damage. After myocardial ischemia, NF-κB (Nuclear factor kappa B) was reported to have either cardioprotective or cardiotoxic effects. Prolonged activation of NF-κB appeared to be cardiotoxic in heart failure by inducing signaling cascades triggering chronic inflammation. Inhibition of NF-κB activation was demonstrated to be less susceptible to I/R. In this context, injury was more dominant from reperfusion than that from ischemia and release of inflammatory substances was thought to be one important cause of reperfusion-associated pathologies, such as cardiomyocyte death, contraction band necrosis, reduced reflow and ventricular arrhythmia.

Experimental studies in animals indicated that therapeutic interventions for example with anti-inflammatory compounds might contribute to a reduction of infarct size and attenuation of cardiac dysfunction. And after myocardial infarction occurred, restoration of blood flow was considered for being the best effective way to save the myocardium from ischemic damage. However, predicting when myocardial infarction occurs and preventing the infarction with long-time use of such compounds is usually not a practical and convenient way for successfully treating infarction.

There is still a need for therapeutically effective compounds and, thus, improved ways for successfully treating I/R injuries, especially myocardial ischemia reperfusion injuries. As usual, it is generally desirable to have compounds with reduced risk for side effects, which can be prepared in a cost-effective way.

Traditional Chinese medicines based on plant materials as well as plants or respective components gained from plants usually allow for treatment of various diseases and conditions while bearing a reduced risk for side effects. In view of the rich medicinal plant resources available respective medicines can usually be produced in a cost-effective way. Accordingly, there has been a lot of research with regard to plants and respective ingredients for treatment of several diseases and conditions.

For example, *Erigeron multiradiatus* (Lindl.) Benth, is a biennial or perennial herb and distributed mainly in the Qinhai-Tibet plateau of China at altitudes ranging from 2600 to 4300 meters. In traditional Tibetan medicine, *E. multiradiatus* has been used for years for the treatment of diseases including hypopepsia, enteritis, diarrhea, food poisoning as well as fever and cough. Studies of phytochemistry reported that flavonoids, phenolic acids and sterols are presented abundantly in this plant. The phenolic acids of *E. multiradiatus* were under investigation, both in phytochemical and bioactive studies. It has been reported that usual or crude extracts of this plant with increased content of flavonoids may have several pharmacological effects including anti-inflammatory ones (e.g. Luo, P. et al., J Ethnopharmacol, 2008, 119:232-237).

The inventors unexpectedly found that a caffeoylquinic acid-rich extract obtained from this plant comprising a mixture of certain caffeoylquinic acids namely a mixture of certain dicaffeoylquinic acids, tricaffeoylquinic acids and Erigoster-based ones proved to be exceptionally efficacious and, thus, provides a highly promising treatment option for treatment of I/R injuries. While several phytochemical and pharmacological aspects of some caffeoylquinic acids isolated from other plants than *E. multiradiatus* or synthetic ones have been provided and respective effects have been evaluated so far (dos Santos et al., Nat Prod Commun, 2010, 5:733-740, Han et al., Neuroscience, 2010, 169:1039-1045, dos Santos et al., Eur J Pharm Sci, 2005, 26: 62-70, Chiou et al., Evid Based Complement Alternat Med, 2011, 634502, doi: 10.1093/ecam/nep140. Epub 2011 Jun. 18), such evaluation did not focus on possible effects of caffeoylquinic acids in *E. multiradiatus*, and, hence, of those caffeoylquinic acids on I/R injuries.

SUMMARY OF THE INVENTION

The present invention provides in a first aspect a process for producing a caffeoylquinic acid-rich extract from plant material of *E. multiradiatus*. Said caffeoylquinic acid-rich extract comprises
at least one compound A of formula (I):

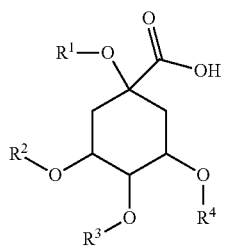

Formula (I)

wherein $R^1$, $R^2$, $R^3$ and $R^4$ are independently from each other selected from hydrogen or a group of Formula (II) with the provisio that two of $R^1$, $R^2$, $R^3$ and $R^4$ are a group of Formula (II);

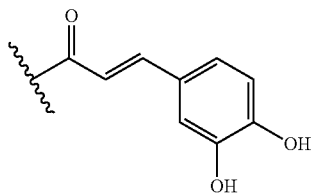

Formula (II)

or derivates of said compound A;

at least one compound B of formula (I), wherein $R^1$, $R^2$, $R^3$ and $R^4$ are independently from each other selected from hydrogen or a group of Formula (II) with the provisio that three of $R^1$, $R^2$, $R^3$ and $R^4$ are a group of Formula (II); or derivates of said compound B; and at least one compound C of Formula (III)

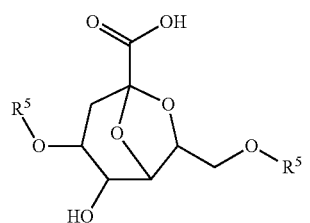

Formula (III)

wherein $R^5$ is a group of Formula (II); or derivates of said compound C.

Said caffeoylquinic acid-rich extract comprises a total amount of compounds A, B and C of at least 15% by weight based on the weight of the caffeoylquinic acid-rich extract, i.e. based on the total weight of said caffeoylquinic acid-rich extract.

Said process for producing the caffeoylquinic acid-rich extract comprises the steps of:
a) treating plant material of *E. multiradiatus* with an extraction solvent at a temperature above 30° C. to produce a crude extract;
b) at least partly separating the compounds A, B and C from said crude extract to obtain a caffeoylquinic acid-rich extract, which step comprises contacting the crude extract with a macroporous adsorbent resin and eluting said resin with at least three different eluting solvents having successively increased amounts of an alcohol (% by volume).

In further aspects, the present invention refers to the caffeoylquinic acid-rich extract obtainable and obtained, respectively, from said process.

Still further, the present invention provides a pharmaceutical formulation comprising the caffeoylquinic acid-rich extract obtained or obtainable by the process described above and pharmaceutically tolerable excipients.

In still a further aspect, the present invention provides a method for treating or preventing a disease caused by myocardial ischemia or myocardial ischemia-reperfusion, said method comprises applying a therapeutically effective amount of the caffeoylquinic acid-rich extract obtainable or obtained by the process described above to a subject. Still further, the invention refers to the use of said caffeoylquinic acid-rich extract in the manufacture of a medicament for the treatment or prevention of myocardial ischemia or myocardial ischemia-reperfusion injuries. Another aspect concerns the use of said caffeoylquinic acid-rich extract for the treatment of myocardial ischemia or myocardial ischemia-reperfusion injuries.

The caffeoylquinic acid-rich extract of the present invention advantageously attenuates myocardial injury which is assumed to be achieved by a reduction of infarct size, suppression of ST-segment depression and decrease in cardiomyocyte necrosis. The caffeoylquinic acid-rich extract of the invention also allows for an exceptional inhibition of leukocyte infiltration and decrease of pro-inflammatory cytokines, inhibition of NF-κB activation and attenuation of JNK (c-Jun N-terminal kinases) phosphorylation. The caffeoylquinic acid-rich extract of the invention, hence, is exceptionally suitable to suppress cardiac inflammatory response and alleviate myocardial I/R injury. It is assumed that the specific composition, namely the presence of certain dicaffeoylquinic acids, tricaffeoylquinic acids and Erigoster-based caffeoylquinic acids contributes to these advantageous therapeutic effects. A synergistic effect of the dicaffeoylquinic acids, tricaffeoylquinic acids and Erigoster-based caffeoylquinic acids claimed might further explain the exceptional effects of said extract.

The present invention also provides a method for treating or preventing a disease caused by myocardial ischemia-reperfusion comprising applying a therapeutically effective amount of certain caffeoylquinic acids, namely caffeoylquinic acids selected from the group of compounds of Formula (IV) to (IX) as recited below and mixtures thereof to a subject. Further in accordance with the present invention is a caffeoylquinic acid selected from the group of said compounds for use in the treatment or prevention of myocardial ischemia-reperfusion injury. Furthermore, the use of a caffeoylquinic acid selected from the group of said compounds in the manufacture of a medicament for the treatment or prevention of myocardial ischemia-reperfusion injury as well as the use of a caffeoylquinic acid selected from the group of said compounds for the treatment of myocardial ischemia-reperfusion injury is an aspect of the present invention.

The technical terms used in this patent application have the meaning as commonly understood by a respective skilled person unless specifically defined.

BRIEF DESCRIPTION OF DRAWINGS

FIG. 3A shows the ST amplitude changes in ECG of the rats after treatment with 10 mg/kg, 20 mg/kg and 40 mg/kg of a caffeoylquinic acid-rich extract of the invention, compared with 5 mg/kg CAPE, saline group (I/R Vehicle) and untreated group (Sham) (n=10/group. * $P<0.05$, **$P<0.01$, vs. Sham, #$P<0.05$, ##$P<0.01$ vs. I/R Vehicle).

FIG. 3B shows the heart rate of rats after treatment with 10 mg/kg, 20 mg/kg and 40 mg/kg of a caffeoylquinic acid-rich extract of the invention compared with 5 mg/kg CAPE, saline group (I/R Vehicle) and untreated group (Sham) (n=10/group. * $P<0.05$, **$P<0.01$, vs. Sham, #$P<0.05$, ##$P<0.01$ vs. I/R Vehicle).

FIG. 5A shows the TNF-α level in cardiac tissue of rats after treatment with 10 mg/kg, 20 mg/kg and 40 mg/kg of a caffeoylquinic acid-rich extract of the invention compared with 5 mg/kg CAPE, saline group (I/R Vehicle) and untreated group (Sham) (n=5/group, **$P<0.01$, vs. Sham, #$P<0.05$ vs. I/R Vehicle).

FIG. 5B shows the IL-6 level in cardiac tissue of rats after treatment with 10 mg/kg, 20 mg/kg and 40 mg/kg of a caffeoylquinic acid-rich extract of the invention compared with 5 mg/kg CAPE, saline group (I/R Vehicle) and untreated group (Sham) (n=5/group, **$P<0.01$, vs. Sham, #$P<0.05$ vs. I/R Vehicle).

FIG. 6A refers to a western blot pattern showing the expressions of phosphor-NF-κB p65 9p65=p-65 of Nuclear factor kappa B), NF-κB p65, I-κB (I-κB=Inhibitor of kappa B), phosphor-JNK and JNK of rats after treatment with 10 mg/kg, 20 mg/kg and 40 mg/kg of a caffeoylquinic acid-rich extract of the invention compared with 5 mg/kg CAPE, saline group (I/R Vehicle) and untreated group (Sham). Normalization of Western blot was ensured by β-actin.

FIG. 6B shows the relative expression of phosphor-NF-κB p65 of rats after treatment with 10 mg/kg, 20 mg/kg and 40 mg/kg of a caffeoylquinic acid-rich extract of the invention compared with 5 mg/kg CAPE, saline group (I/R Vehicle) and untreated group (Sham) (**$P<0.01$, vs. Sham, ##$P<0.01$, #$P<0.05$ vs. I/R Vehicle).

FIG. 6C shows the relative expression of I-κB of rats after treatment with 10 mg/kg, 20 mg/kg and 40 mg/kg of a caffeoylquinic acid-rich extract of the invention compared with 5 mg/kg CAPE, saline group (I/R Vehicle) and untreated group (Sham) (**$P<0.01$, vs. Sham, #$P<0.01$, #$P<0.05$ vs. I/R Vehicle).

FIG. 6D shows the relative expression of phosphor-JNK of rats after treatment with 10 mg/kg, 20 mg/kg and 40 mg/kg of a caffeoylquinic acid-rich extract of the invention compared with 5 mg/kg CAPE, saline group (I/R Vehicle) and untreated group (Sham) (**$P<0.01$, vs. Sham, ##$P<0.01$, #$P<0.05$ vs. I/R Vehicle).

DESCRIPTION OF THE EMBODIMENTS

Figure 1:
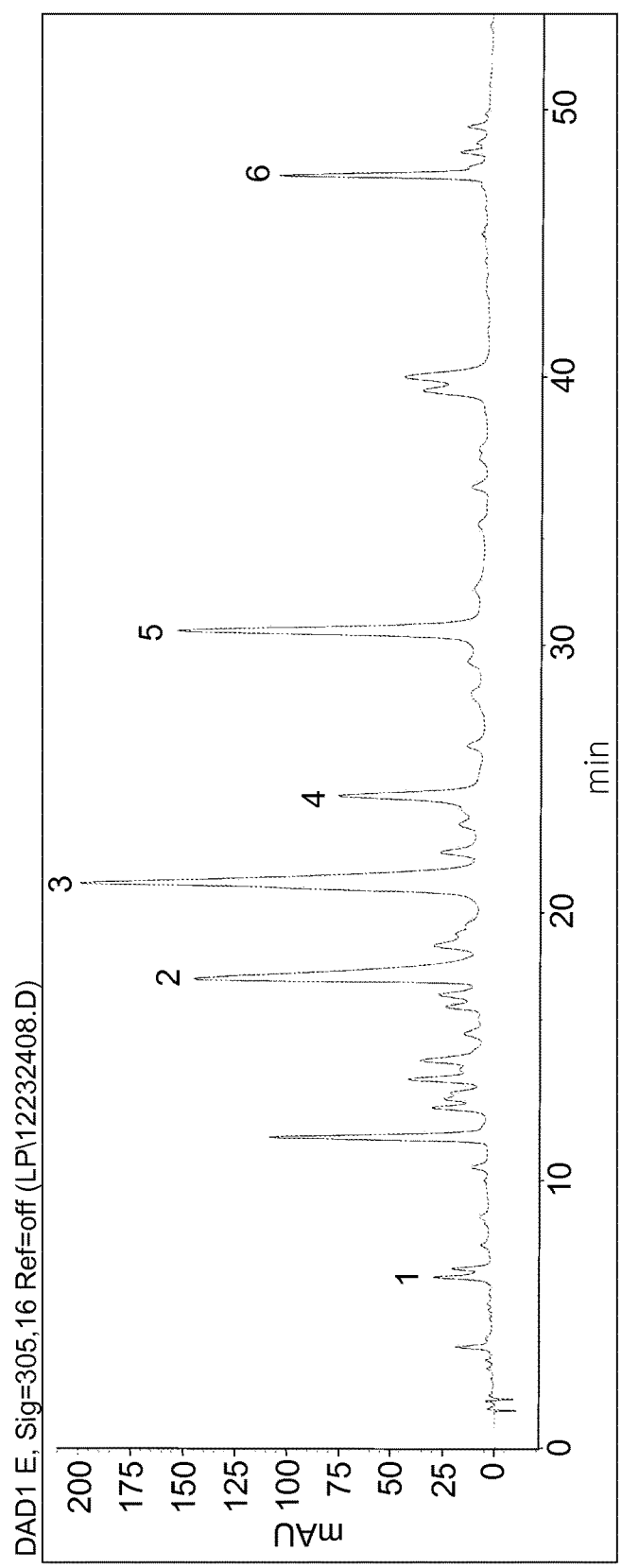
FIG. 1 refers to a HPLC chromatogram showing the major caffeoylquinic acids of the caffeoylquinic acid-rich extract of example 1, namely 1,3-dicaffeoylquinic acid (1) corresponding to Formula (VIII) as recited below, 3,4-dicaffeoylquinic acid (2) corresponding to Formula (VI) as recited below, 3,5-dicaffeoylquinic acid (3) corresponding to Formula (IV) as recited below, 4,5-dicaffeoylquinic acid (4) corresponding to Formula (VII) as recited below, 3,4,5-tricaffeoylquinic acid corresponding to Formula (V) as recited below (5) and Erigoster B corresponding to Formula (IX) as recited below (6).

The present invention refers in a first aspect to a process for producing a caffeoylquinic acid-rich extract from plant material of E. multiradiatus. The extract according to the present invention is a caffeoylquinic acid-rich one, i.e. said extract has an increased amount of caffeoylquinic acids, in particular an amount of more than 50% by weight of caffeoylquinic acids based on the weight of the caffeoylquinic acid-rich extract. Preferably, said caffeoylquinic acid-rich extract is an extract having more than 60% by weight, more preferably more than 70% by weight, still more preferably more than 75% by weight and especially preferably at least 80% by weight of caffeoylquinic acids based on the weight of the caffeoylquinic acid-rich extract. The skilled person is aware how to determine and measure the amount of caffeoylquinic acids. The method given in the Chinese pharmacopeia (referenced as "appendix VA") and UV-VIS spectrophotometer assay, respectively, is preferably used for determining the amount of caffeoylquinic acids. For example, the absorption can be measured at 305 nm using a UV-VIS spectrophotometer assay, wherein the results are expressed as g of 1,3-dicaffeoylquinic acid equivalent (corresponding to a compound of Formula (VIII)/100 g extract.

The term "caffeoylquinic acids" is known to the skilled person and refers to phenolic compounds and phenylpropanoids, respectively. Caffeoylquinic acids have been reported to exist in and to be derivable from several plants. The term "caffeoylquinic acids" preferably includes the compounds determined with the above referenced method.

Caffeoylquinic acids generally comprise or are derived from quinic acid (tetrahydroxycyclohexanecarboxylic acid, Formula A) linked to caffeic acid (3-(3,4-Dihydroxyphenyl)-2-propenoic acid, Formula B). Hence the term caffeoylquinic acids include compounds comprising structural components of Formula (A) and (B), wherein both are directly linked, or are compounds with structural components being derived from and related to structural components of Formula (A) and (B), respectively, being directly linked:

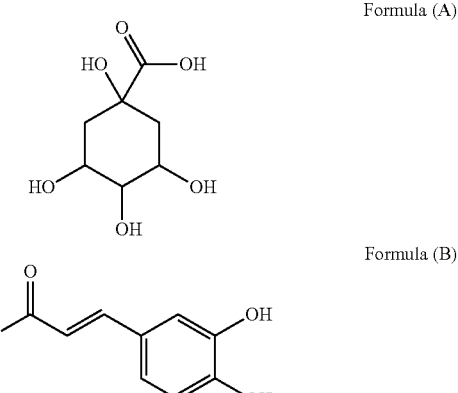

Formula (A)

Formula (B)

Caffeoylquinic acids are usually classified according to the number and the position of caffeoyl moieties. Caffeoylquinic acids, for example, include monocaffeoylquinic acids with quinic acid moiety and one caffeoyl moiety, dicaffeoylquinic acids with quinic acid moiety and two caffeoyl moieties, tricaffeoylquinic acids with quinic acid moiety and three caffeoyl moieties and multicaffeoylquinic acids with quinic acid moiety and more than three caffeoyl moieties as well as compounds therefrom. The latter includes, for example, isomers and alkylesters of mono-, di- or tricaffeoylquinic acids.

In the present invention, derivates of structural components of Formula (A) are considered for covering structural components of Formula (C) and (D), too, both considered for being related to quinic acid according to the present invention. Hence, further examples of derivates referred to as "caffeoylquinic acids" according to this invention are compounds having one of the following structural components and which are directly linked to at least one structural component of Formula (B) or derived from Formula (B):

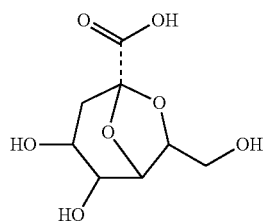

Formula (C)

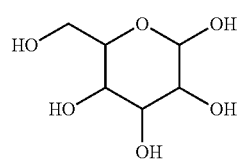

Formula (D)

The term "caffeoylquinic acids" according to the present invention preferably refers to Compounds comprising and more preferably consisting of structural components of Formula (A) and (B) being directly linked in particular by ester bond, wherein the compounds have at least one structural component of Formula (B), namely one, two, three or more than three structural components of Formula (B) and preferably have one structural component of Formula (A); as well as esters, preferably alkyl esters of these compounds; and Compounds comprising and more preferably consisting of structural components of Formula (C) or (D) and at least one structural component of Formula (B), namely one, two, three or more than three structural components of Formula (B) and preferably have one structural component of Formula (C) or (D), wherein structural component of Formula (C) or (D) is directly linked to structural component of Formula (B) in particular by ester bond; and esters, preferably alkyl esters of these compounds.

The term "caffeoylquinic acids" according to the invention especially comprises and at least refers to compounds A, B and C further described below.

The caffeoylquinic acid-rich extract comprises at least one compound A of formula (I):

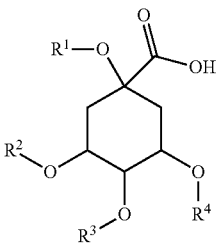

Formula (I)

wherein $R^1$, $R^2$, $R^3$ and $R^4$ are independently from each other selected from hydrogen or a group of Formula (II) with the provisio that two of $R^1$, $R^2$, $R^3$ and $R^4$ are a group of Formula (II);

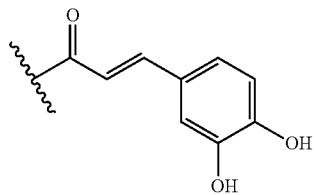

Formula (II)

or derivates of said compound A.

Said caffeoylquinic acid-rich extract additionally comprises at least one compound B of formula (I), wherein $R^1$, $R^2$, $R^3$ and $R^4$ are independently from each other selected from hydrogen or a group of Formula (II) with the provisio that three of $R^1$, $R^2$, $R^3$ and $R^4$ are a group of Formula (II); or derivates of said compound B.

Said caffeoylquinic acid-rich extract also comprises at least one compound C of Formula (III)

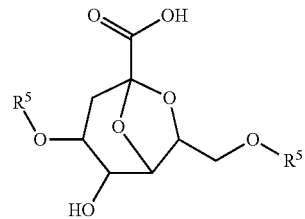

Formula (III)

wherein $R^5$ is a group of Formula (II); or derivates of said compound C.

Thus, the caffeoylquinic acid-rich extract according to the invention comprises at least one compound A as defined above being a dicaffeoylquinic acid, at least one compound B as defined above being a tricaffeoylquinic acid and at least one compound C as defined above being based on Erigoster, which structure is known to the skilled person. The total amount of compounds A, B and C in said extract is at least 15% by weight based on the weight of the caffeoylquinic acid-rich extract. More preferably, the total amount of compounds A, B and C in said extract is at least 20% by weight, in particular at least 22% by weight and especially preferably at least 25% by weight based on the weight of the caffeoylquinic acid-rich extract. In preferred embodiments, said caffeoylquinic acid-rich extract comprises at least one compound A of formula (I) as recited above with $R^1$, $R^2$, $R^3$ and $R^4$ being independently from each other selected from hydrogen or a group of Formula (II) and with the provisio that two of $R^1$, $R^2$, $R^3$ and $R^4$ are a group of Formula (II) recited above; and said extract further comprises at least one compound B of formula (I) as recited above with $R^1$, $R^2$, $R^3$ and $R^4$ being independently from each other selected from hydrogen or a group of Formula (II) and with the provisio that three of $R^1$, $R^2$, $R^3$ and $R^4$ are a group of Formula (II); and wherein said extract also comprises at least one compound C of Formula (III) as recited above with $R^5$ being a group of Formula (II).

The amount of the compound A is preferably at least 10% by weight based on the weight of the caffeoylquinic acid-rich extract. More preferably, the compound A is present in an amount of at least 12% by weight, still more preferably in an amount of at least 15% by weight based on the weight of the caffeoylquinic acid-rich extract. Compound A preferably comprises a compound of Formula (IV)

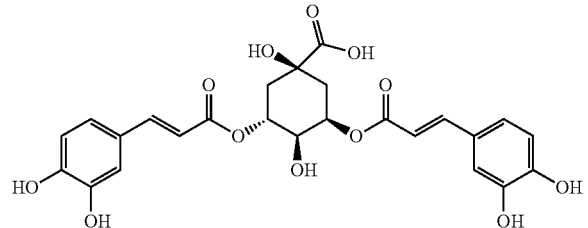

Formula (IV)

The amount of said compound of Formula (IV) is preferably at least 7% by weight, more preferably at least 8% by weight, still more preferably at least 9.5% by weight based on the weight of the caffeoylquinic acid-rich extract.

The amount of the compound B is preferably at least 5% by weight based on the weight of the caffeoylquinic acid-rich extract. The compound B is more preferably present in an amount of at least 6% by weight, still more preferably in an amount of at least 6.5% by weight based on the weight of the caffeoylquinic acid-rich extract. Compound B preferably comprises a compound of Formula (V)

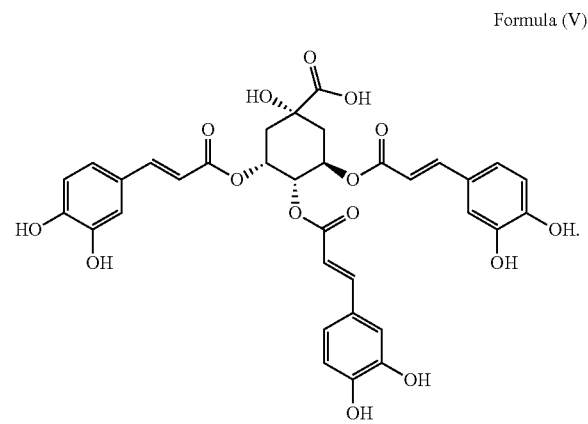 [SMILES: O=C(/C=C/c1ccc(O)c(O)c1)O[C@@H]1C[C@](O)(C(=O)O)C[C@@H](OC(=O)/C=C/c2ccc(O)c(O)c2)[C@H]1OC(=O)/C=C/c1ccc(O)c(O)c1]

Formula (V)

The amount of said compound of Formula (V) is preferably at least 4% by weight, more preferably at least 5% by weight and still more preferably at least 6.5% by weight based on the weight of the caffeoylquinic acid-rich extract.

The compound C is preferably present in an amount of at least 1% by weight, still more preferably in an amount of at least 2% by weight based on the weight of the caffeoylquinic acid-rich extract.

In an especially preferred embodiment of this invention, the amount of compound of Formula (IV) in the caffeoylquinic acid-rich extract provided by said process is preferably at least 8% by weight and the amount of the compound of Formula (V) is at least 5% by weight based on the weight of the caffeoylquinic acid-rich extract, wherein the total amount of compounds A, B and C in said embodiment is at least 20% by weight based on the weight of the caffeoylquinic acid-rich extract.

Especially preferably, the caffeoylquinic acid-rich extract comprises each of compounds of Formulas (IV) to (IX):

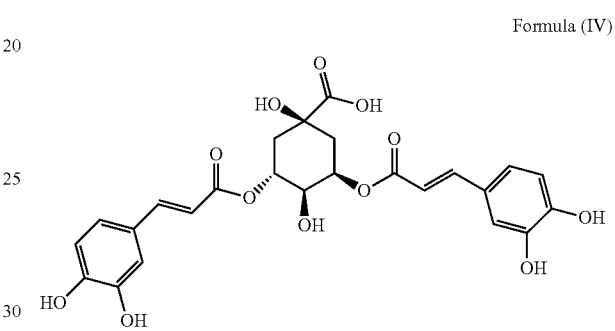

Formula (IV)

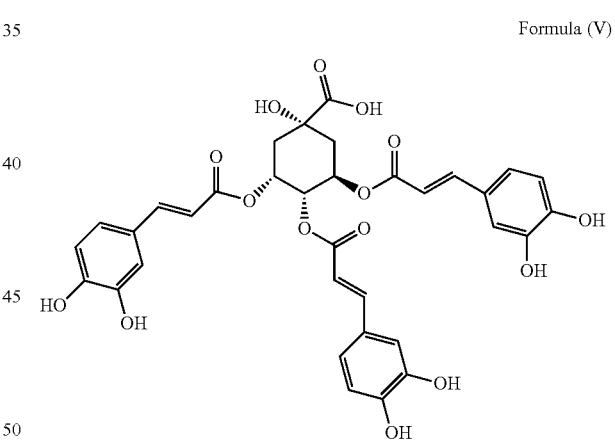

Formula (V)

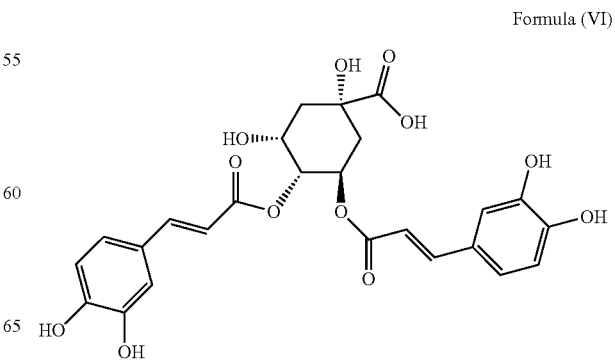

Formula (VI)

-continued

Formula (VII)

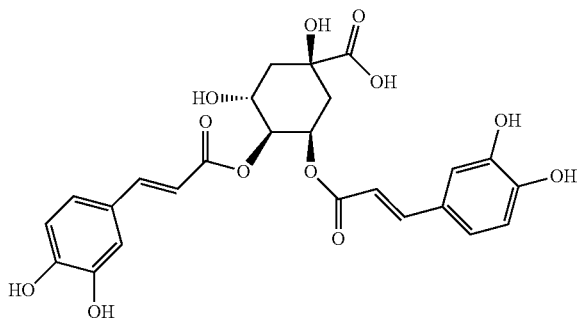

Formula (VIII)

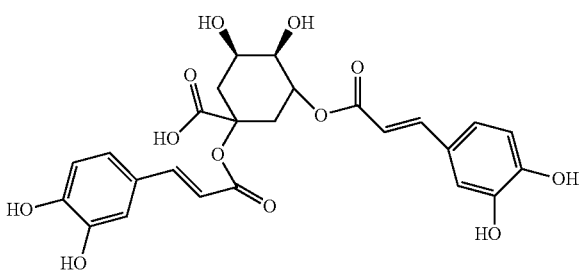

Formula (IX)

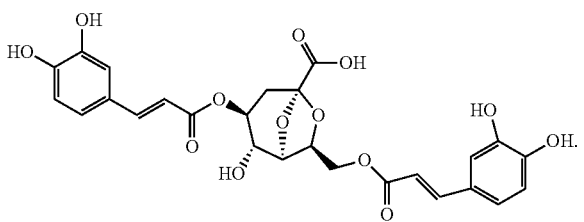

In such preferred embodiments of the invention, compound A comprises compounds of Formula (IV), (VI), (VII) and (VIIII), compound B comprises a compound of Formula (V) and compound C comprises a compound of Formula (IX).

Still more preferably, said caffeoylquinic acid-rich extract comprises each of compounds of Formulas (IV) to (IX) as recited above with the following amounts:

Compound of Formula (IV) in an amount of at least 8% by weight, preferably of at least 9.5% by weight, more preferably in an amount of about 10.4% by weight;

Compound of Formula (V) in an amount of at least 5% by weight, preferably at least 6.5% by weight, more preferably in an amount of about 7.2% by weight;

Compound of Formula (VI) in an amount of at least 2% by weight, preferably at least 3% by weight, more preferably in an amount of about 3.8% by weight;

Compound of Formula (VII) in an amount of at least 1% by weight, preferably at least 1.5% by weight, more preferably in an amount of about 2.1% by weight;

Compound of Formula (VIII) in an amount of at least 0.2% by weight, preferably at least 0.5% by weight, more preferably in an amount of about 0.7% by weight; and Compound of Formula (IX) in an amount of at least 1% by weight, preferably at least 1.5% by weight, more preferably in an amount of about 2.7% by weight.

The process for producing the caffeoylquinic acid-rich extract according to the present invention comprises the steps of:

a) treating plant material of *E. multiradiatus* with an extraction solvent at a temperature above 30° C. to produce a crude extract;

b) at least partly separating compounds A, B and C from said crude extract to obtain a caffeoylquinic acid-rich extract, which step comprises contacting the crude extract with a macroporous adsorbent resin and eluting said resin with at least three different eluting solvents having successively increased amounts of an alcohol (% by volume).

Macroporous adsorbent resins are known to the skilled person and the skilled person is able to select suitable macroporous adsorbent resins for carrying out the inventive process. Suitable macroporous adsorbent resins especially include HPD100. Preferably, the macroporous adsorbent resin is a macroporous adsorbent resin column.

The extraction solvent in step a) comprises an organic solvent, usually an alcohol, preferably an aliphatic alcohol. The alcohol may be selected from the group consisting of methanol, ethanol, propanol, butanol and mixtures thereof. More preferably the alcohol is ethanol. Especially preferably, the extraction solvent is 75% (by volume) ethanol.

The plant material is preferably extracted for at least 1 h, in particular for at least 1.5 h and especially preferably for at least 2 h with said extraction solvent. Preferably, the extraction is carried out under reflux conditions, i.e. as reflux extraction. The extraction in step a) can be carried out by treating the plant material at least two times, in particular at least three times with the extraction solvent at a temperature above 30° C., wherein preferably the same type of extraction solvent is used. More preferably, all extraction steps are carried out with an extraction solvent comprising ethanol, still more preferably with 75% (% by volume) ethanol.

The fluid obtained after the at least one extraction and in particular at least two or three extraction steps in step a) is preferably filtered and the filtrate is preferably evaporated to obtain the crude extract. The filtration in step a) can be carried out by centrifuge filtration. The at least three different eluting solvents having successively increased amounts of alcohol (% by volume) used in step b) preferably comprise at least one eluting solvent with an amount of an alcohol of more than 50% (% by volume; also referenced as "high alcohol eluting solvent").

The at least three different eluting solvents having successively increased amounts of alcohol (% by volume) used in step b) still more preferably comprise:

A first eluting solvent, which first eluting solvent preferably consists of water;

A second eluting solvent preferably comprising water and an amount of less than 50% of an alcohol (by volume). The alcohol is preferably ethanol. More preferably the second eluting solvent is 40% (by volume) ethanol.

A third eluting solvent preferably comprising water and an amount of more than 50% of an alcohol (by volume). The alcohol is preferably ethanol. More preferably the third eluting solvent is 60% (by volume) ethanol.

Said first eluting solvent is preferably used in a first step for eluting the macroporous adsorbent resin to form a first fraction, subsequently the resin is eluted with the second eluting solvent to form a second fraction and after eluting the resin with said second eluting solvent, the third eluting solvent is applied for eluting the resin to form a third fraction. Preferably, step b) further comprises a step of collecting the eluent obtained from the elution with the high alcohol eluting solvent, in particular the third eluting solvent (also referenced as "high alcohol fraction eluent" and "third fraction eluent", respectively) and preferably subjecting said high alcohol fraction eluent, in particular the third fraction eluent, to a further purification step for obtaining the caffeoylquinic acid-rich extract. Said further purification step in step b) preferably comprises removing the alcohol from the high alcohol fraction eluent, in particular the third fraction eluent, to form a residue (also references as "high alcohol fraction residue" and "third fraction residue", respectively). In preferred embodiments, said high alcohol fraction residue, in particular the third fraction residue, is extracted, preferably with an organic ester, more preferably an aliphatic ester. Said organic ester is in particular ethyl acetate (acetic ether).

In preferred embodiments, said high alcohol fraction residue, in particular the third fraction residue, is extracted at least two times with said organic ester, especially preferably ethyl acetate, more preferably at least three times. The fluid obtained after extracting said high alcohol fraction residue, in particular the third fraction residue, is preferably concentrated and dried to form the caffeoylquinic acid-rich extract.

In one embodiment of the invention, the inventive process further comprises a step of drying and pulverizing the plant material of E. multiradiatus to form a powder before step a) is carried out. The plant material used is preferably derived from the whole plant of E. multiradiatus.

In a further aspect, the present invention provides the caffeoylquinic acid-rich extract obtainable from the process described above. The invention also provides the caffeoylquinic acid-rich extract obtained from the process described above.

The invention further provides a method for treating or preventing a disease caused by myocardial ischemia or myocardial ischemia-reperfusion. Said method comprises applying a therapeutically effective amount of the caffeoylquinic acid-rich extract of the present invention to a subject. The subject may be a mammal. The mammal may be a rodent such as a rat. In particular embodiments of the invention, the mammal is a human.

Said disease is preferably caused by myocardial ischemia-reperfusion. The effective amount of said extract is preferably administered to the subject after myocardial infarction and before the blood reflow. Such administration after myocardial infarction and just before the blood reflow provides further advantageous and proved to be a highly effective way to treat myocardial I/R injury.

The caffeoylquinic acid-rich extract may be applied in an amount of at least 10 mg/kg, preferably at least 20 mg/kg. Said amount applied refers to the amount of caffeoylquinic acid-rich extract in mg per kg body weight of the subject. In further embodiments, the caffeoylquinic acid-rich extract is applied in an amount of at least 40 mg/kg. Doses preferably administered to rodents such as rats may include 10 mg/kg, 20 mg/kg and 40 mg/kg, usually 20 mg/kg and 40 mg/kg, in particular 40 mg/kg of the caffeoylquinic acid-rich extract.

The caffeoylquinic acid-rich extract may be administered by any administration way including oral, rectal, topical, parenteral or transdermal or inhalative administration. The caffeoylquinic acid-rich extract can be administered in a therapeutically effective amount by single bolus injection, in particular in a vein. The caffeoylquinic acid-rich extract of the invention can be applied in combination with other active compounds, especially those being used for treatment of heart diseases.

In preferred embodiments, the method of the invention comprises applying a therapeutically effective amount of the caffeoylquinic acid-rich extract which extract comprises At least one compound A of formula (I) as recited above with $R^1$, $R^2$, $R^3$ and $R^4$ being independently from each other selected from hydrogen or a group of Formula (II) and with the provisio that two of $R^1$, $R^2$, $R^3$ and $R^4$ are a group of Formula (II) recited above.

At least one compound B of formula (I) as recited above with $R^1$, $R^2$, $R^3$ and $R^4$ being independently from each other selected from hydrogen or a group of Formula (II) and with the provisio that three of $R^1$, $R^2$, $R^3$ and $R^4$ are a group of Formula (II); and At least one compound C of Formula (III) as recited above with $R^5$ being a group of Formula (II).

In further preferred embodiments, the method comprises applying a therapeutically effective amount of the caffeoylquinic acid-rich extract comprising a compound A comprising a compound of Formula (IV) as recited above and a compound B comprising a compound of Formula (V) as recited above, wherein the amount of said compound of Formula (IV) is at least 8% by weight and the amount of said compound of Formula (V) is at least 5% by weight based on the weight of the caffeoylquinic acid-rich extract.

The caffeoylquinic acid-rich extract applied in the method preferably has a total amount of compounds A, B and C of at least 20% by weight based on the weight of the caffeoylquinic acid-rich extract.

Still more preferably, the caffeoylquinic acid-rich extract applied in the method comprises each of compounds of Formulas (IV) to (IX) as recited above, wherein in especially preferred embodiments said caffeoylquinic acid-rich extract comprises each of these compounds with the following amounts:

Compound of Formula (IV) in an amount of about 10.4% by weight;
Compound of Formula (V) in an amount of about 7.2% by weight;
Compound of Formula (VI) in an amount of about 3.8% by weight;
Compound of Formula (VII) in an amount of about 2.1% by weight;
Compound of Formula (VIII) in an amount of about 0.7% by weight; and
Compound of Formula (IX) in an amount of about 2.7% by weight.

Such composition proved to be especially advantageous regarding its therapeutic effects.

In a further aspect of the invention, a pharmaceutical formulation comprising the caffeoylquinic acid-rich extract according to the invention and pharmaceutically tolerable excipients is provided. The skilled person is aware of suitable excipients for preparing pharmaceutical formulations. Pharmaceutical formulations of the invention include tablets, capsules, powder, liquid preparations such as liquids for injection, implants or external preparations. In particular embodiments, the pharmaceutical formulation is a liquid preparation, especially a liquid preparation for injection.

In still another aspect, the invention provides said caffeoylquinic acid-rich extract described above or said pharmaceutical formulation described above comprising the caffeoylquinic acid-rich extract of the invention for use in the treatment or prevention of myocardial ischemia or myocardial ischemia-reperfusion injuries, preferably of myocardial ischemia-reperfusion injury. Still further, the invention refers to the use of said caffeoylquinic acid-rich extract described above in the manufacture of a medicament for the treatment or prevention of myocardial ischemia or myocardial ischemia-reperfusion injuries, preferably of myocardial ischemia-reperfusion injury. Another aspect of the present invention concerns the use of said caffeoylquinic acid-rich extract for the treatment of myocardial ischemia or myocardial ischemia-reperfusion injuries, preferably of myocardial ischemia-reperfusion injury. Possible subjects, doses and ways for administrating as well as preferred compositions of the caffeoylquinic acid-rich extract are those described above.

Still a further aspect of the present invention refers to a method for treating or preventing a disease caused by myocardial ischemia-reperfusion comprising applying a therapeutically effective amount of a caffeoylquinic acid selected from the group of compounds of Formula (IV) to (IX) as recited above and mixtures thereof to a subject. Further in accordance with the present invention is a caffeoylquinic acid selected from the group of compounds of Formula (IV) to (IX) and mixtures thereof for use in the treatment or prevention of myocardial ischemia-reperfusion injury. Furthermore, the use of a caffeoylquinic acid selected from the group of compounds of Formula (IV) to (IX) and mixtures thereof in the manufacture of a medicament for the treatment or prevention of myocardial ischemia-reperfusion injury as well as the use of a caffeoylquinic acid selected from the group of compounds of Formula (IV) to (IX) and mixtures thereof for the treatment of myocardial ischemia-reperfusion injury is an aspect of the present invention.

The inventors assume that the exceptional therapeutic effects of the caffeoylquinic acid-rich extract and its main components of the invention in a disease caused by myocardial ischemia or myocardial ischemia-reperfusion is mainly based on an advantageous decrease in myocardial infarct size, reduction of CK-MB and LDH activities, prevention in ST-segment depression, reduction of cardiac tissue levels of pro-inflammatory factors TNF-$\alpha$ and IL-6, attenuation of leukocyte infiltration and inhibition of I-$\kappa$B degradation and nuclear translocation of p-65 as well as attenuation of phosphorylation of JNK. The compounds A, B and C, in particular compounds (IV) to (IX) are assumed to be the main and active components contributing to the advantageous pharmacological effects of the caffeoylquinic acid-rich extract.

The examples set out below further illustrate the invention. The preferred embodiments described above and the drawing as well as examples given below represent preferred or exemplary embodiments and a skilled person will understand that the reference to those embodiments or examples is not intended to be limiting.

EXAMPLES

A caffeoylquinic acid-rich extract from *E. multiradiatus* has been prepared and its effects on acute myocardial infarction, especially I/R injuries have been evaluated in rats.

The whole plant of *E. multiradiatus* (Family: Asteraceae) was collected in Ganzi, Sichuan Province, China, and identified by Hao Zhang, Professor of Taxonomy and Pharmaceutical Botany in Pharmacy School of West China, Sichuan University. The voucher specimen (E12025) was deposited in the herbarium of pharmacy school of West China, Sichuan University.

Standards of 1,3-dicaffeoylquinic acid, 3,4-dicaffeoylquinic acid, 3,5-dicaffeoylquinic acid, 4,5-dicaffeoylquinic acid, 3,4,5-tricaffeoylquinic acid and Erigoster B (purity>98%) were purchased from National Institute for Food and Drug Control (NIFDC, Beijing, China). Acetonitrile was HPLC grade and deionized water was prepared using a Millipore water purification system. Caffeic acid phenethyl ester (CAPE) was from Sigma-Aldrich (purity>97%). Polyclonal rabbit anti-mouse phosphor-NF-$\kappa$B, I-$\kappa$B$\alpha$ and phosphor-JNK antibodies were purchased from Cell Signaling Technology or BD Transduction Laboratories. 2,3,5-triphenyltetrazolium chloride (TTC) was purchased from Sigma (St. Louis, Mo., USA). Creatine kinase-MB (CK-MB) and Lactate dehydrogenase (LDH) kits were purchased from STANBIO (Texas, USA).

Adult male Sprague-Dawley (SD) rats weighting 220-280 g were purchased from the Animal House, Pharmacy Discipline, Sichuan University (Chengdu, P.R. China). The animals were fed individually under constant temperature (25±1° C.) and humidity with a 12 h light/dark cycle and with a rodent standard diet with free access water ad libitum. Animal care and treatment procedures were in accordance with the Institutional Guidelines and Animal Ordinance, which was approved by the local Animal Ethics Committees of the Faculty of Medicine, Sichuan University.

Data were expressed as mean±S.E.M. Significance was determined by one-way analysis of ANOVA using SPSS 16.0 software (SPSS, Inc., Chicago, Ill., USA). For single and multifactorial analysis, post-hos test(s) were performed to measure individual group differences of interest. Differences were considered significant if $p<0.05$.

Example 1

Preparation of a Caffeoylquinic Acid-Rich Extract and Chemical Analysis

The dried herb of *E. multiradiatus* (2.0 kg) was ground to powder, and then reflux-extracted with 75% ethanol (% by volume) for three times (3×12 L, 2 h each), then membrane filtered through centrifuge, and the filtrate solution was evaporated to obtain (396.5 g) crude extract. The crude extract was enriched by macroporous adsorbent resin. The resin column was successively eluted by three eluting solvents, namely by water, 40% ethanol (% by volume) and 60% ethanol (% by volume). Then, the 60% ethanol eluate was collected and concentrated under the vacuum to remove ethanol. The residual was extracted for three times with ethyl acetate (acetic ether). Then the acetic ether solutions were concentrated and dried to obtain a caffeoylquinic acid-rich extract (7.2 g).

The total caffeoylquinic acid content of the extract was determined by referring to the method of the Chinese pharmacopeia. The absorption was measured in quartz well at 305 nm using a UV-VIS spectrophotometer assay (Shimadzu, Japan). The results were expressed as gram 1,3-dicaffeoylquinic acid equivalent/100 g extract. The calibration equation for 1,3-dicaffeoylquinic acid was $y=8.6942 x+0.02318$ ($R2=0.9992$) within the concentration range of 10-120 μg/mL.

HPLC analysis experiments were performed on an Agilent 1200 HPLC system (Agilent Technologies, USA) with diode array detector. An Agilent C18 column (150 mm×4.6 mm, 5 μm) was used to separate the compound. The gradient elution was performed with a flow rate of 1.0 ml/min. The wavelengths were set at 305 nm. The column temperature was set at 25° C. The mobile phase consisted of 0.1% aqueous acetic acid and acetonitrile and the injection volume was 10 μl. The gradient elution program was as follows: 0-40 min, 13-25% acetonitrile; 40-50 min, 25-40% acetonitrile; 50-60 min 40-50% acetonitrile. The content of total "caffeoylquinic acids" according to the invention as measured by UV-VIS spectrophotometer assay was 81.7% based on the weight of the caffeoylquinic acid-rich extract. The presence of specific caffeoylquinic acids of Formulas (IV) to (IX) has been confirmed by HPLC (FIG. 1).

The results demonstrated that the major constituents were 1,3-dicaffeoylquinic acid (0.7%) corresponding to Formula (VIII) as recited above, 3,4-dicaffeoylquinic acid (3.8%) corresponding to Formula (VI) as recited above, 3,5-dicaffeoylquinic acid (10.4%) corresponding to Formula (IV) as recited above, 4,5-dicaffeoylquinic acid (2.1%) corresponding to Formula (VII) as recited above, 3,4,5-tricaffeoylquinic acid (7.2%) corresponding to Formula (V) as recited above and Erigoster B (2.7%) corresponding to Formula (IX) as recited above, respectively.

Example 2

Cardioprotective Effects of a Caffeoylquinic Acid-Rich Extract of the Invention

An ischemia reperfusion injury was produced in rat heart based on Buerke's description with our modifications (Buerke et al., Proc Natl Acad Sci USA, 1995, 92:8031-8035). Sixty rats were randomly divided into six groups (n=10 per group): (I) Sham group (given saline vehicle without I/R); (II) I/R group with saline alone; (III) I/R group with 10 mg/kg of the caffeoylquinic acid-rich extract of example 1; (IV) I/R group with 20 mg/kg of the caffeoylquinic acid-rich extract of example 1; (V) I/R group with 40 mg/kg of the caffeoylquinic acid-rich extract of example 1; (VI) I/R group with CAPE caffeic acid phenylethyl ester, 2-phenylethyl (2E)-3-(3,4-dihydroxyphenyl)acrylate) 5 mg/kg as positive control.

CAPE was well-demonstrated to be a potent anti-inflammatory and anti-oxidant natural component. Previous preclinical studies have further confirmed cardioprotective effects of CAPE treatment including effects on I/R injured hearts.

The vehicle or drugs were administered 1 min before reperfusion via single bolus tail vein injection. Rats were anesthetized with pentobarbital sodium (70 mg/kg body weight) by an i.p. injection of a mixture of 20% Dorminal (1 ml contains 200 mg pentobarbital sodium, Alfasan) and sterile saline at a ratio of 1:3 (VN). Using a PowerLab (ADInstruments Pty Ltd., Castle Hill, Australia), mean aortic pressure (MAP) was recorded from the Millar catheter. Electrocardiogram (ECG) in lead II was also recorded through the needle electrodes attached to the limbs. The heart rate and ST-segment elevation were calculated off-line. The chest was opened at the left fourth intercostal space. The pericardium was incised and the left atrium appendage was elevated to expose the LAD (Left anterior descending coronary artery occlusion) coronary artery. A 6-0 silk suture was passed around the LAD coronary artery, and the ends of the suture were threaded through a small vinyl tube to form a snare. Ischemia was established by tightening the suture from both ends with fixed weight. The animals then underwent 30 min of ischemia, confirmed visually in situ by the appearance of regional epicardial cyanosis and ST-segment elevation. Reperfusion was introduced by releasing the snare gently for a period of 90 min. Sham group rats were subjected to the entire surgical procedures above except the introduction of LAD ligation and release. Then, blood was collected from orbital veins at 24 h after I/R and serum was separated by centrifugation (4000 rpm, 5 min) for LDH and CK-MB assay. After collection of serum samples, 2 ml of ice-cold 10% potassium chloride was injected via inferior vena cava to stop the heart in diastole and the heart was excised and weighted immediately. The left ventricle was excised for infarct size measurement or was frozen in liquid nitrogen before being stored at −80° C.

This study comparing the efficacy of 3 doses of a caffeoylquinic acid-rich extract of the invention (10, 20 and 40 mg/kg) with CAPE at 5 mg/kg and saline regarding acute myocardial I/R injury in rats confirmed that the caffeoylquinic acid-rich extract of the invention had a higher efficacy than CAPE. The six caffeoylquinic acids identified above appear to be major and active compounds accounting for the observed cardioprotection of the caffeoylquinic acid-rich extract against I/R injury.

The caffeoylquinic acid-rich extract of example 1 proved to allow for an exceptional inhibition of I/R-induced injury as indicated by a decrease in myocardial infarct size, reduction of CK-MB and LDH activities and prevention in ST-segment depression. Said caffeoylquinic acid-rich extract further resulted in an advantageous reduction of cardiac tissue levels of pro-inflammatory factors TNF-α and IL-6 and attenuation of leukocyte infiltration. Additionally, the caffeoylquinic acid-rich extract demonstrated to significantly inhibit I-κB degradation and nuclear translocation of p-65 and attenuate phosphorylation of JNK. Hence, a caffeoylquinic acid-rich extract according to the invention provides potent cardioprotection and, thus, is highly effective for treating myocardial I/R injury by a mechanism that could be due to an exceptional anti-inflammatory activity of said extract.

Example 2a

Decrease in Myocardial Infarct Size

Measurement of heart infarct size was performed by TTC staining method as described previously (Zhou et al., J Ethnopharmacol, 2011, 135:287-298). The left ventricle was cut perpendicular to the base-apex axis into six 2-3 mm slices. The slices were incubated in 1% TTC solution in PBS (pH 7.4) for 5 min at 37° C. and then fixed in 10% formalin solution (pH 7.0) for 20-24 h. TTC stains viable tissue a deep red color and nonstained tissue is presumed to be infarcted. The images of the slice were captured by a LEICA digital camera 480 and infarct area in each slice was measured by computed planimetry with an image analyzing program Image J1.26 (Wayne Rasband, National Institutes of Health, USA). Then the infarct area of each slice was determined by manual delineation of TTC-negative pale area of the image. The infarct weight of each slice was calculated by multiplying the ratio of infarct area within total area by the slice weight. The infarct weight of each slice was summed to produce the total infarct weight of each left ventricle. Finally, the infarct size was calculated by dividing the total infarct weight of each left ventricle by the total weight of the ventricle.

Figures 2A, 2B, 2C:
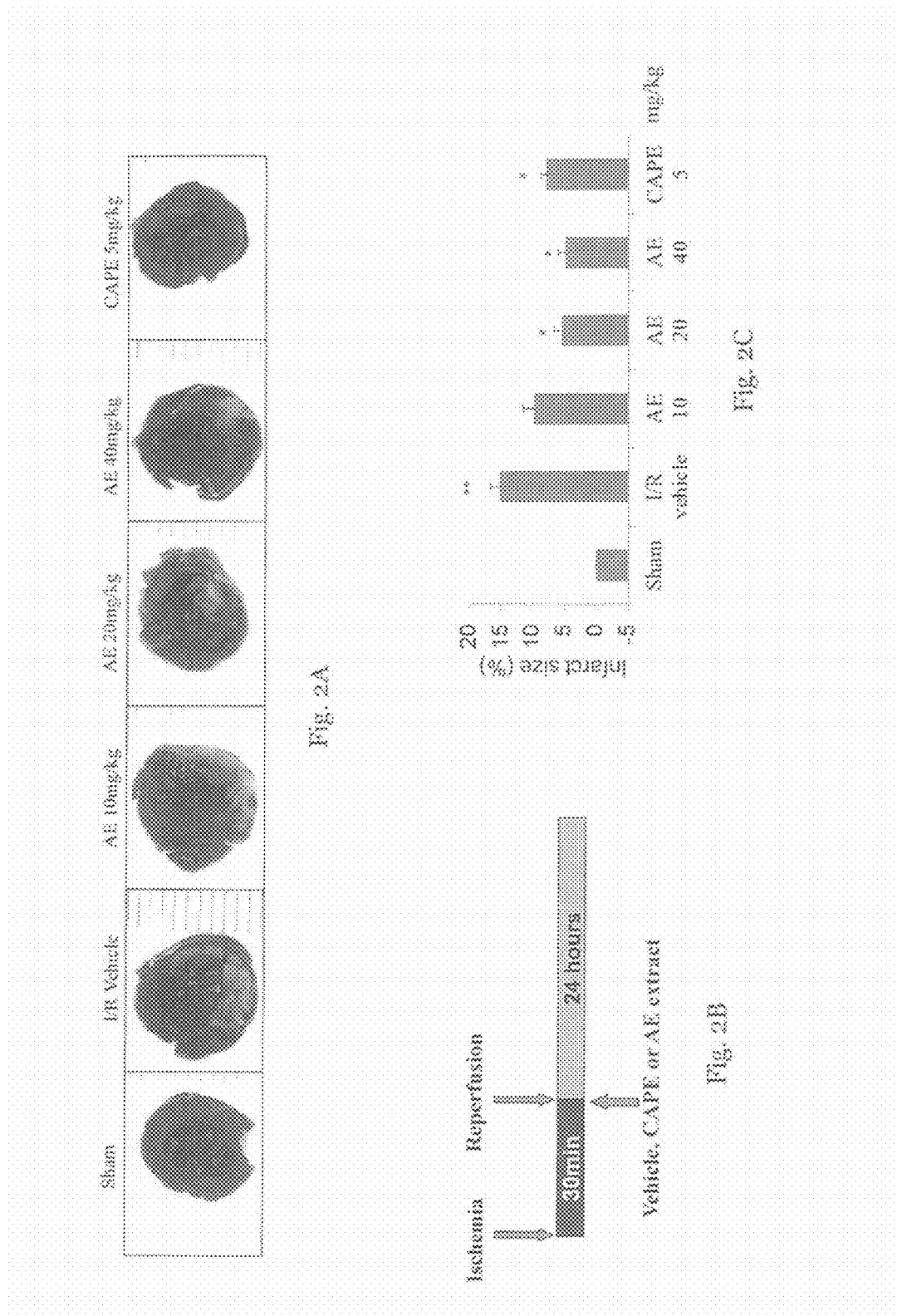
FIG. 2A shows the TTC stained left ventricle slices of a rat treated with different concentrations of a caffeoylquinic acid-rich extract of the invention, namely 10 mg/kg, 20 mg/kg and 40 mg/kg compared with the TTC stained left ventricle slices of an untreated rat (Sham), a rat treated with saline (I/R Vehicle) and a rat treated with 5 mg/kg caffeic acid phenethyl ester (CAPE, positive control). Deep red-staining areas indicate normal tissue and unstained pale areas indicate infarct tissue.
FIG. 2B is a schematic diagram showing the experimental procedures for evaluating the effects of a caffeoylquinic acid-rich extract, CAPE (positive control) and saline (vehicle) on the myocardial infarct size after ischemia and reperfusion.
FIG. 2C shows the myocardial infarct sizes of rats after treatment with 10 mg/kg, 20 mg/kg and 40 mg/kg of a caffeoylquinic acid-rich extract of the invention compared with 5 mg/kg CAPE (positive control), saline group (I/R Vehicle) and untreated group (Sham) (myocardial infarct size determined by TTC staining, n=5/group. **$P<0.01$, vs. Sham, #$P<0.05$ vs. I/R Vehicle).

To evaluate the effect of the caffeoylquinic acid-rich extract of example 1 against myocardial ischemia, it has been determined whether said extract was effective at ameliorating myocardial infarction after I/R. SD rats were subjected to 30 min ischemia followed by 24 h of reperfusion (FIG. 2B). The caffeoylquinic acid-rich extract of example 1 at 3 different dosages, CAPE (positive control) or saline (vehicle) was injected intravenously via the tail vein 1 min before reperfusion. The infarct sizes were significantly decreased in subjects treated with 20 and 40 mg/kg of a caffeoylquinic acid-rich extract of example 1 compared with the vehicle-treated group (5.4±1.3%, 4.9±1.1%, vs 15.2±1.4% vehicle, p<0.05). The low dosage caffeoylquinic acid-rich extract at 10 mg/kg also decreased the infarct size but the reduction did not reach a statistical significance. Administration of CAPE afforded significant reduction with the infarct size at 7.9±0.9%. These results confirm that the caffeoylquinic acid-rich extract of the invention reduced myocardial infarct size after I/R injury in a dose-dependent manner (FIG. 2C).

Example 2b

Prevention of ST Segment Depression and Inhibition of Heart Rate Decrease 24 h after I/R, all rats were anesthetized with sodium pentobarbital (40 mg/kg) through intraperitoneal injection. Electrocardiogram (ECG) in lead II was recorded through the needle electrodes attached to the limbs continuously for 15 min with an electrocardiograph (ASB240U, AOSHENG, China). The heart rate and ST-segment depression were calculated off-line.

The caffeoylquinic acid-rich extract of example 1 suppressed I/R-induced ST-segment depression. The amplitude of ST-segment and heart rate were recorded and used as the index of ischemic electrocardiograph changes. The total mV of ST-depression (ΣSTamp) was approximately 0.2 mV in the anesthetized rats after I/R, indicating a markedly ischemia as compared with rats with sham operation (FIG. 3A). Administration of the caffeoylquinic acid-rich extract of example 1 at 20 and 40 mg/kg significantly inhibited 24 h reperfusion-induced ST-segment depression. CAPE (5 mg/kg) also showed significant protective effects against the I/R-induced ST-segment depression. Heart rate was decreased after 24 h reperfusion in the vehicle-treated rats, as compared to Sham group (FIG. 3B). Similar to the case of ST-depression, the caffeoylquinic acid-rich extract of example 1 at 40 mg/kg inhibited the heart rate decrease significantly. The caffeoylquinic acid-rich extract of example 1 at 10 mg/kg or 20 mg/kg had no effect, and CAPE had a slight effect without significant difference. There results confirm that the caffeoylquinic acid-rich extract of the invention exerts potent protective effects on the ischemic electrocardiography changes induced by 30 min ischemia and 24 h reperfusion in rats.

Example 2c

Reduction of CK-MB and LDH Activities

Figure 4:
FIG. 4 shows the Creatine kinase-MB (CK-MB) and Lactate dehydrogenase (LDH) activities in serum of rats after treatment with 10 mg/kg, 20 mg/kg and 40 mg/kg of a caffeoylquinic acid-rich extract of the invention compared with 5 mg/kg CAPE, saline group (I/R Vehicle) and untreated group (Sham) (n=5/group. **$P<0.01$, vs. Sham, #$P<0.05$, ##$P<0.01$ vs. I/R vehicle).

At 24 h after I/R, the blood was collected and centrifuged for 15 min at 4° C., 3000 g and the serum was stored at −80° C. until assayed for cytokines. Activities of LDH and CK-MB were determined by using commercial assay kits according to manufacturer's instructions. Both, the serum levels of CK-MB and LDH, as two markers of myocardial necrosis, were significantly increased in vehicle-treated rats after I/R (FIG. 4). The caffeoylquinic acid-rich extract of example 1 at 20 mg/kg (975±26.6 vs. 1375±56.8 U/L for CK-MB, $P<0.05$; 306±14.7 vs. 465±15.6 U/L for LDH, $P<0.05$) or 40 mg/kg (841±31.2 vs. 1375±56.8 U/L for CK-MB, $P<0.01$; 246±23.5 vs. 465±15.6 U/L for LDH, $P<0.01$) generated a significant decrease in serum CK-MB and LDH levels. The same is true for the CAPE treatment (913±40.2 for CK-MB, $P<0.01$; 287±18.8 for LDH, $P<0.01$). The caffeoylquinic acid-rich extract at a dose of 10 mg/kg did not exhibit significant activity in this assay compared to the I/R vehicle group.

Example 2d

Decrease of Levels of TNF-α and IL-6

At 24 h after I/R, left ventricular tissue samples were collected. Levels of TNF-α and IL-6 were measured using ELISA kits for TNF-α (RayBiotech, Inc., Norcross Ga.) and IL-6 (R & D System). Frozen left ventricular tissues were homogenized using a homogenizer (IKA, Germany) in ice-cold PBS. Homogenates were sonicated and centrifuged (2000 g for 10 min at 4° C.) and resulting supernatants were used for ELISA determination. The contents of total protein in the supernatants were determined by using a Bio-Rad kit (Bio-Rad Laboratories, Hercules, Calif., USA). Cytokine levels were normalized to the equal total protein amount. To determine the effect of a caffeoylquinic acid-rich extract on pro-inflammatory cytokines, cardiac tissue levels of TNF-α and IL-6 after I/R were evaluated. TNF-α and IL-6 levels were significantly elevated in vehicle-treated rats subjected to I/R injury (FIGS. 5A and 5B). Administration of the caffeoylquinic acid-rich extract of example 1 and CAPE markedly decreased levels of TNF-α and IL-6. The caffeoylquinic acid-rich extract of example 1 at 40 mg/kg had significant effects on TNF-α and IL-6 levels, suggesting that the cardioprotective effect may be associated with reduction of pro-inflammatory cytokines.

Example 2e

Inhibition of Activation of NF-κB and I-κB Degradation and Attenuation of Phosphorylation of JNK Western blot analyses of total proteins and phosphorylated form of proteins in hearts were performed according to previously described methods with modifications. Left ventricular tissue were homogenized in ice-cold lysis buffer [Sucrose 250 mM, Tris-HCl (pH 7.2) 50 mM, sodium EDTA 2 mM, Beta-marcoptoethanol 2 mM, sodium fluoride 5 mM, sodium orthovanadate 1 mM, aprotinin 10 μg/ml, leupeptin 10 μg/ml] for 5 min. Equal amounts of protein were separated using 10% SDS polyacrylamide gel and transferred onto Immobilon-P membrane (Pore size: 0.45 μm, Millipore, USA). Rabbit polyclonal antibodies against phospho-JNK, total JNK, phospho-NF-κB p65, total NF-κB, p65 I-κBα and β-actin were used to analyze expression levels of signaling molecules as described. Band intensities were quantified using a densitometer analysis system (Quantity One software, Bio-Rad).

To evaluate the effects of the caffeoylquinic acid-rich extract of the invention on NF-κB pathway, phosphorylation of NF-κB at Ser536 and expression level of I-κB were detected in myocardium after I/R. Western blot analysis showed that I/R markedly up-regulated NF-κB phosphorylation (p-p65) and decreased I-κB as compared with cardiac tissue of rats with sham operation. Treatment with the caffeoylquinic acid-rich extract of the invention (20 mg/kg and 40 mg/kg) inhibited the I/R-induced NF-κB activation and I-κB degradation (FIG. 6A to 6C). The results indicate that the caffeoylquinic acid-rich extract of example 1 especially inhibits NF-κB activation to suppress inflammatory response and survival after myocardial infarction.

The caffeoylquinic acid-rich extract of example 1 further proved to attenuate the phosphorylation of JNK. JNK is a stress-related kinase and its activation is induced by inflammatory stress in numerous types of cells, including cardiomyocytes. The western blot analysis revealed that compared to Sham group, the expression of p-JNK from vehicle-treated group was increased significantly after I/R injury, while there was no difference with regard to the protein level of total JNK (FIGS. 6A and 6D). Administration of the caffeoylquinic acid-rich extract of example 1 (20 mg/kg and 40 mg/kg) and CAPE before reperfusion markedly reduced JNK phosphorylation, suggesting attenuation of JNK subsequent translocation into the nucleus.

Example 2f

Inhibition of Leucocyte Infiltration

Figure 7:
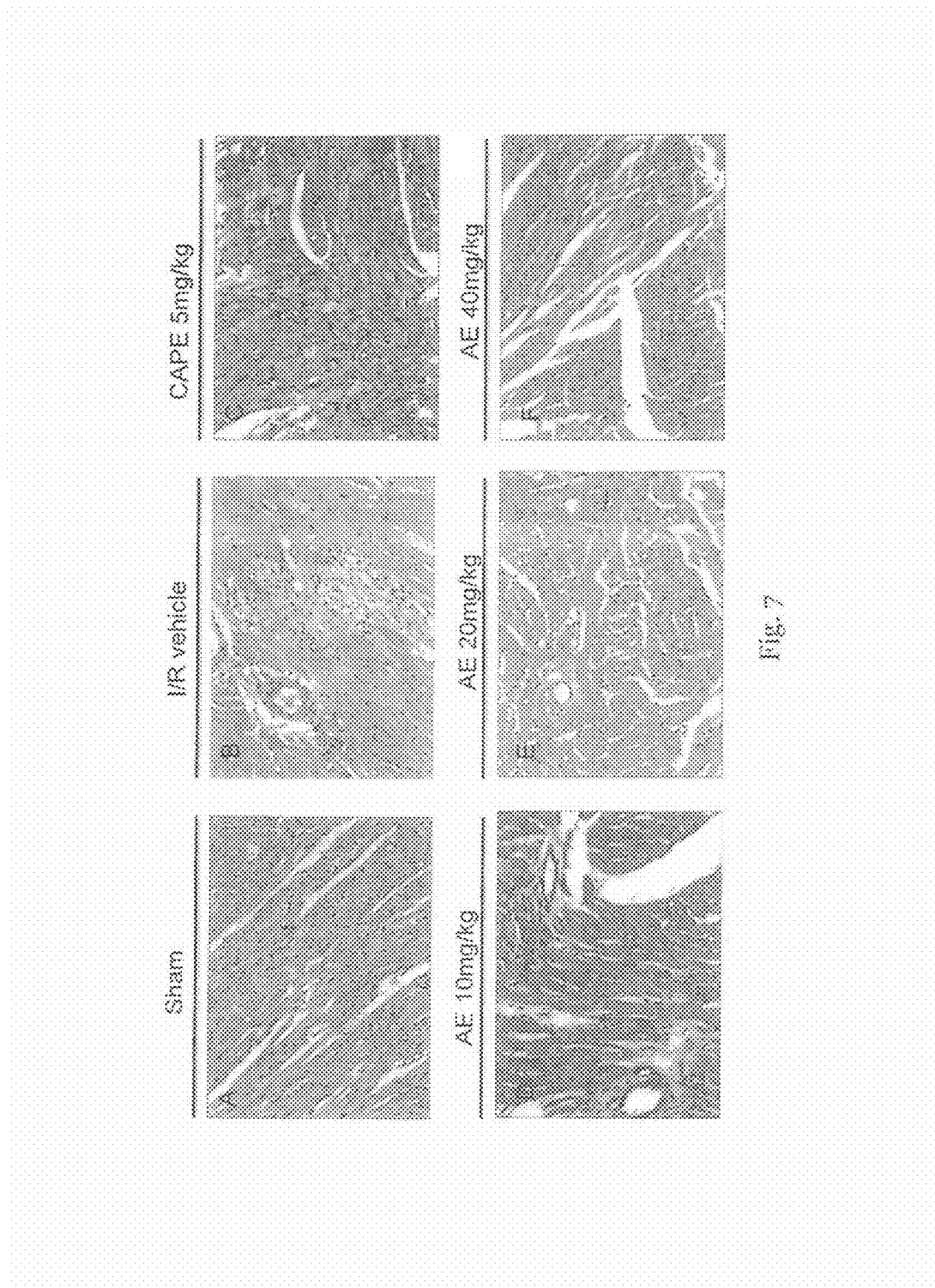
FIG. 7 shows the stained left ventricular sections of rats stained with hematoxylin and eosin after treatment with 10 mg/kg, 20 mg/kg and 40 mg/kg of a caffeoylquinic acid-rich extract of the invention compared with 5 mg/kg CAPE, saline group (I/R Vehicle) and untreated group (Sham) (n=5 in each group).

The caffeoylquinic acid-rich extract of the invention inhibits leukocyte infiltration. Histological analyses of hearts (FIG. 7) demonstrated that I/R induced widespread tissue necrosis in infarct area including leukocyte infiltration, interstitial hypercellularity, contraction bands, capillary compression and abundant signs of hemorrhage (FIG. 7B). Treatment with the caffeoylquinic acid-rich extract of example 1 reduced these I/R-induced hispathological changes and hearts treated at 40 mg/kg appeared normal or there were only few interstitial edema (FIG. 7F). The decreased adherent and infiltrated PMNs (polymorphonuclear leukocytes) in groups treated with the caffeoylquinic acid-rich extract of the invention reflected the anti-inflammatory activity of said extract concerning hearts after I/R.

What is claimed is:

1. A method for treating a disease caused by myocardial ischemia or myocardial ischemia-reperfusion, said method comprising applying a therapeutically effective amount of a caffeoylquinic acid-rich extract from E. multiradiatus to a subject, the extract comprising:
each of compounds (IV) to (IX) as follows (% by weight based on the weight of the caffeoylquinic acid-rich extract):
Compound of Formula (IV)

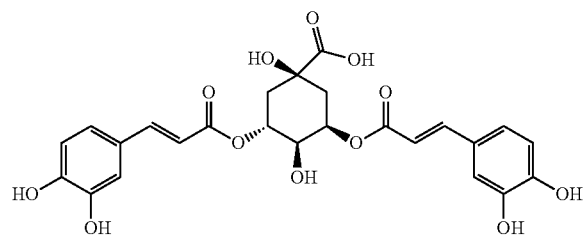

Formula (IV)

in an amount of about 10.4% by weight;

Compound of Formula (V)

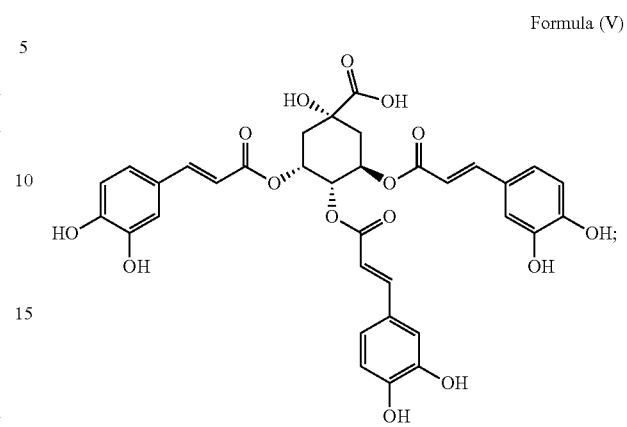

Formula (V)

in an amount of about 7.2% by weight;

Compound of Formula (VI)

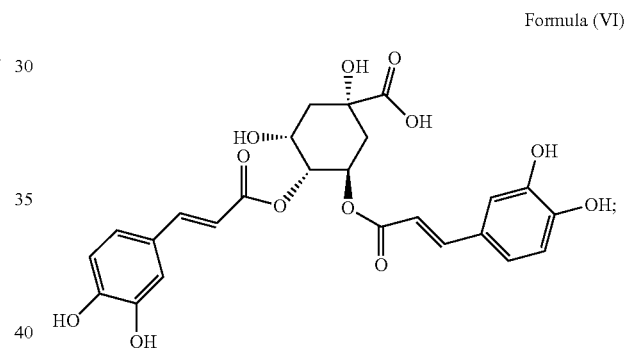

Formula (VI)

in an amount of about 3.8% by weight;

Compound of Formula (VII)

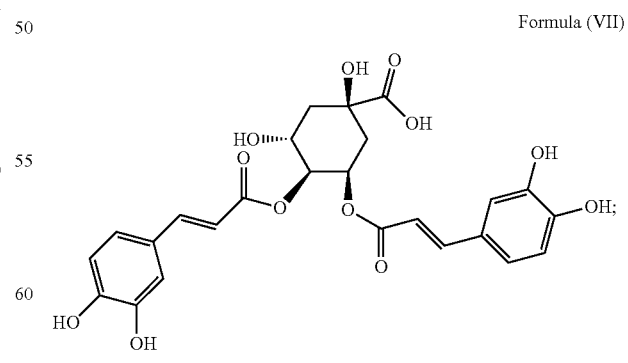

Formula (VII)

in an amount of about 2.1% by weight;

Compound of Formula (VIII)
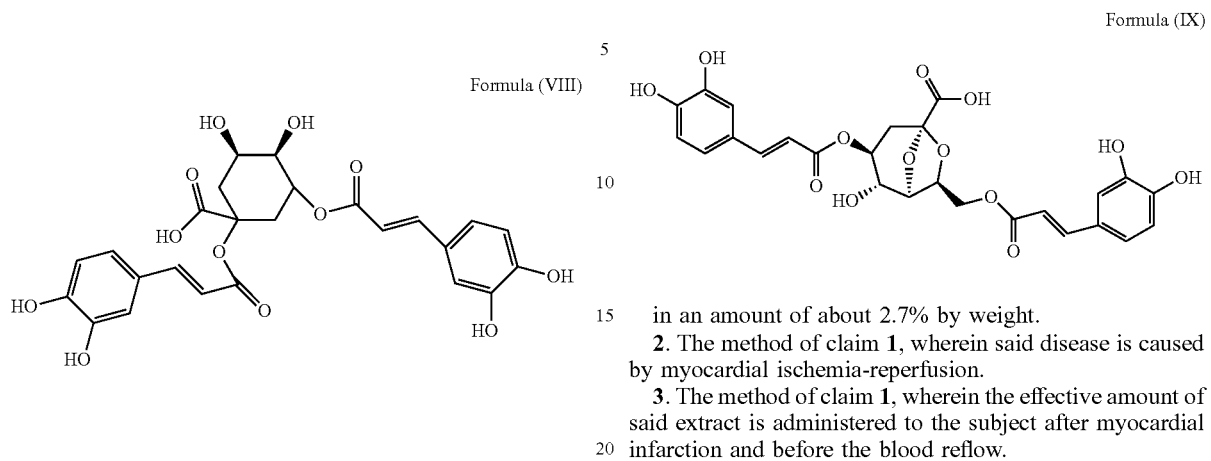
in an amount of about 0.7% by weight; and
Compound of Formula (IX)
in an amount of about 2.7% by weight.
2. The method of claim 1, wherein said disease is caused by myocardial ischemia-reperfusion.
3. The method of claim 1, wherein the effective amount of said extract is administered to the subject after myocardial infarction and before the blood reflow.
* * * * *